United States Patent [19]

Simmons et al.

[11] Patent Number: 5,637,307

[45] Date of Patent: Jun. 10, 1997

[54] METHOD OF IMMERSION STERILIZATION AND ORGANIC COLD CHEMICAL STERILANT

[76] Inventors: Paul L. Simmons, 6250 Kipps Colony Ct., No. 203, Gulfport, Fla. 33707; Robert L. Immekus, 106 E. Hanna Ave., Tampa, Fla. 33604

[21] Appl. No.: 195,365

[22] Filed: Feb. 14, 1994

Related U.S. Application Data

[63] Continuation-in-part of Ser. No. 901,592, Jun. 19, 1992, Pat. No. 5,405,602, which is a continuation-in-part of Ser. No. 642,709, Jan. 17, 1991, Pat. No. 5,145,663, which is a continuation of Ser. No. 304,312, Jan. 31, 1989, abandoned.

[51] Int. Cl.$^6$ .............. A61L 2/18; A61L 2/02; A61K 9/08
[52] U.S. Cl. .............. 424/405; 422/20; 422/28
[58] Field of Search .............. 424/47, 405; 422/20, 422/28

[56] References Cited

U.S. PATENT DOCUMENTS 3,282,775  11/1966  Stonehill ................... 424/36
4,511,486   4/1985  Shah ........................ 424/45

*Primary Examiner*—Edward J. Webman
*Attorney, Agent, or Firm*—A. W. Fisher, III

[57] ABSTRACT

A method of immersion sterilization of medical and dental instruments and an organic cold chemical sterilant capable of killing a challenge of target microorganisms including bacterial spores wherein the method of immersion sterilization comprises the steps of immersion of the instruments in a first organic solution to solubilize the protein of the microorganisms, immersion in an aqueous solution to unprotonate the solubilized proteins and exposing the bioburden on the instruments to ultrasonic agitation to remove organic material from the instruments and immersion in a second organic solution to cross-link the binding sites of the unprotonated proteins thereby denaturing the proteins to corrupt and penetrate the bacterial walls to kill the endospores and other microorganisms; and wherein the organic cold chemical sterilant comprises a monohydric alcohol, a polyhydric alcohol, a dialdehyde, a surface active agent and water in proportion by weight to denature the proteins to corrupt and penetrate the bacterial and conidial walls to kill the endospores and other microorganisms.

8 Claims, No Drawings

METHOD OF IMMERSION STERILIZATION AND ORGANIC COLD CHEMICAL STERILANT

This application is a continuation-in-part application of application Ser. No. 901,592 filed Jun. 19, 1992, now U.S. Pat. No. 5,405,602, that is a continuation-in-part application of application Ser. No. 642,709, filed Jan. 17, 1991, now U.S. Pat. No. 5,145,663, that is a continuation application Ser. No. 304,312 filed Jan. 31, 1989, now abandoned.

BACKGROUND OF THE INVENTION

1. Field of the Invention

A method of immersion sterilization of medical and dental instruments and an organic cold chemical sterilant capable of killing a challenge of target microorganisms including bacterial spores.

2. Description of the Prior Art

Sterilants are used in many areas, such as in the sterilization of laboratory, surgical, dental and other equipment. Since these chemical sterilizing agents or other chemical sterilizing methods commonly take six to ten (6–10) hours to be effective, it is customary in hospital practice to chemically sterilize instruments overnight.

Methods of sterilization involving either the use of pressurized steam, dry heat or ethylene oxide are common. However, some of these methods are cumbersome, tedious and time-consuming employing potential carcinogens, often damage the sterilized material and require expensive equipment and skilled technicians.

Moreover, steam or heat sterilization is impracticable for many plastic devices and delicate instruments which are sensitive to elevated temperatures.

Many chemical sterilization methods have been developed as substitutes for steam or heat sterilization. Unfortunately most have shortcomings. Phenols, ketones and formaldehyde compositions have considerable sporicidal activity but have objectionable odors and extreme toxicity. Ethanol, isopropyl alcohol and the quaternary ammonium compounds have been used, and though less odorous and toxic, lack the activity or efficacy of the phenols and formaldehyde compositions.

Compositions comprising saturated dialdehydes with alkalinating agents have also been used. Though such compounds are satisfactory as chemical sterilization agents their sporicidal activity is limited to certain pH ranges, require up to ten (10) hours to effectively kill the pathogens, and have certain limits on stability.

U.S. Pat. No. 3,282,775 shows a sporicidal composition including saturated dialdehydes preferably glutaraldehyde from 0.1 percent to 2.0 percent containing from 2 to 6 carbon atoms and a cationic surface active agent. The compounds may be diluted either with water or lower alkanols such as methanol, ethanol, isopropanol and the like, or with combinations to form aqueous-alcohol solutions in a 30 percent to 60 percent ratio. The deleterious effects of lower alkanols on rubber, plastics and cements as well as corrosion are recognized. The addition of anti-corrosion agents are therefore suggested.

U.S. Pat. No. 4,040,977 describes a preservative and disinfecting composition for aqueous emulsions, suspensions and solutions which are obtained by reaction in water of a haloacetamide or thiocyanoacetamide or mixture thereof; an alcohol or mixture of alcohols; and formaldehyde.

U.S. Pat. No. 3,697,222 describes a sterilization process achieved by contacting a contaminated object with an aqueous acid glutaraldehyde solution at temperatures above about 45 degrees C. The high temperature precludes the use of alcohol due to the dangers of explosion and rapid evaporation and increase the irritating effect of the vapor. The sterilizing action may be promoted by ultrasonic energy.

U.S. Pat. No. 4,093,744 teaches a means for killing spores on instruments and the like utilizing the combination of glutaraldehyde and a detergent selected from the group consisting of nonionic, anionic and ampholytic surface active agents preferably in an aqueous solution.

U.S. Pat. No. 4,048,336 relates to a means for killing spores on instruments and the like utilizing the combination of glutaraldehyde and a monoaldehyde such as formaldehyde.

U.S. Pat. No. 4,208,404 shows an aqueous solution of glutaraldehyde of acid pH value with dissolved quantities of certain highly ionized salts to kill dormant spores at room temperature.

U.S. Pat. No. 3,016,328 teaches a dialdehyde alcoholic sporicidal composition including of about 0.01 percent to about 1.0 percent saturated dialdehyde, about 60 percent to about 70 percent lower alkanol and an alkalinating agent.

U.S. Pat. No. 4,294,797 describes a composition to sterilize medical instruments comprising an alcohol-aldehyde active substance combination in a proportion of 5 to 15 percent by weight. The preferred alcohol is isopropanol and the preferred aldehyde is formaldehyde or a succinic acid dialdehyde complex and the preferred ratio of alcohol to aldehyde is one to one.

U.S. Pat. No. 2,889,243 shows a chemical composition having antiviral activity comprising hydroxpyruvaldehyde ether as the active ingredient together with water and a surface active agent.

U.S. Pat. No. 4,173,653 teaches an oxydiacetaldehyde as an active antimicrobial agent in an aqueous solution for disinfecting or sterilizing. The activity against bacteria or spores can be improved by adding alkalinating agents or alcohols or propylene glycol or by raising pH or temperature.

U.S. Pat. No. 4,923,899 describes an aqueous composition for killing bacteria, spores, fungi and viruses on nonabsorbent surfaces comprising at least one quaternary ammonium salt, at least one aliphatic dialdehyde having from two to six carbon atoms, and at least one aliphatic hydroxyl compound having from one to eight atoms. Optionally, a chelating agent and an inorganic nitrite salt may be employed.

U.S. Pat. No. 3,968,250 describes a method for disinfecting or sterilizing medical, surgical, dental instruments or other objects in liquid phase by combining nonionic and anionic surfactants with aqueous alcoholic glutaraldehyde solutions. The method can be used also with ultrasonic irradiation over a wide frequency range of from 10 to 850 kHz. The test examples show that the composition is ineffective with ultrasonic agitation or heat unless the concentration of glutaraldehyde is relatively high. The use of heat also limits the percentage of alcohol that can be used leaving the percentage of water relatively high. The example of the alcohol/water composition consists of 60 percent isopropyl alcohol and 37.8 percent water. Moreover, the effectiveness of cationic agents is denegrated. U.S. Pat. Nos. 3,968,248 and 3,912,450 teach similar methods.

U.S. Pat. No. 4,103,001 claims a room temperature aqueous sterilizing composition comprising from 0.75 percent by weight of glutaraldehyde and from 4–15 percent by weight of phenol and a metal phenate, preferably sodium phenate. Optionally present are 1–5 percent by weight of sodium tetraborate, 2–10 percent by weight of a humectant such as glycerol, di-ethylene glycol or propylene glycol and a surfactant.

U.S. Pat. No. 4,511,486 discloses a foamable aqueous liquid denture cleanser and deodorant comprising a surfactant, humectant, water and ethanol or isopropanol with a preferred ration percentage by weight of about 1, 6.5, 29, 1 and 61 respectively.

U.S. Pat. No. 4,923,899 teaches an aqueous sterilant composition wherein the preferred embodiment consists of cloride/bromide/nitrate (21%), isopropyl alcohol (14%), propylene glycol (12%) and water (balance %). The use of glutaraldehyde (2.6%–3.2%) is also disclosed.

Various spray germicides for sanitizing such surfaces is typified by U.S. Pat. No. 3,445,564. U.S. Pat. No. 3,445,564 is directed to a method, compositions and articles for sanitizing public or communal facilities prior to individual use. The method consists of applying a thin layer of a rapidly drying liquid germicidal composition to a surface such as a toilet seat. The rapidly drying germicidal compositions consist essentially of a lower aliphatic alcohol and at least about 5 percent of a volatizing agent such as acetone. Isopropyl alcohol has excellent germicidal activity and is sufficiently volatile to give a satisfactory drying rate when blended with suitable proportions of a volatizing agent. Although the isopropyl alcohol-acetone composition of U.S. Pat. No. 3,445,564 has germicidal activity against bacteria, fungi and other lower organisms, additional antibacterial, antifungal or other active ingredients may be incorporated to enhance the overall germicidal effectiveness. Suitable germicidal additives include the well known antibacterial quaternary ammonium compound. In essence, U.S. Pat. No. 3,445,564 teaches the use of isopropyl alcohol to kill a limited number of germs on a dry toilet seat with the addition of acetone to volatize an already highly volatile chemical to rapidly dry the toilet seat for use within 30 seconds.

U.S. Pat. No. 4,678,658 shows an aerosol spray for use in disinfecting a surface for personal use such as a public restroom facility or telephone. The composition and delivery of the compositions provides for the placement of a spray of disinfectant which includes a dye that disappears as the spray effects the germicidal activity of the disinfectant. The composition is also rapidly drying, so that the dye disappears as well as the disinfecting composition leaving the surface dry. However, the spray is corrosive and environmentally unsafe.

U.S. Pat. No. 3,821,413 discloses a formulation of materials which permits an effective, uniform rate of evaporation of glycols from an air circulator device to reduce airborne bacteria in the surrounding atmosphere. It was observed that the relative amounts and identities of the components of the formulation are critical to the attainment of the desired continuous evaporation of glycols over a prolonged period of time.

The composition of U.S. Pat. No. 3,821,413 is a single phase liquid composition especially adapted for volatilization at a substantially uniform rate from the air circulator device. Generally speaking, the composition includes three essential components (1) a glycol, (2) an organic polar coupling compound for maintaining the homogeneity prevents the glycol from separating from the mixture during evaporation of the mixture into the atmosphere and (3) an organic, relatively non-polar compound for forming hydrophobic micelles with the glycol molecules in the resulting mixture for reducing the affinity of the glycol to atmospheric moisture and thereby increasing the rate at which the glycol may be evaporated into the atmosphere.

The affinity of glycols to attract atmospheric moisture significantly reduces their volatility and impairs their evaporation rate. Accordingly, the compositions of the invention include from about 5 percent to about 80 percent by weight of an organic, relatively non-polar compound for forming hydrophobic micelles surrounding the glycol molecules in the mixture for reducing the affinity of the glycol to atmospheric moisture and thereby increase the rate of evaporation of the glycol. Without this micelle formation, it was found that the glycol or mixture of glycols in the mixture cannot evaporate appreciably in an air circulator device containing a wick immersed in the liquid composition.

U.S. Pat. No. 3,806,593 is directed to an acne treatment medication applied to the skin for preventing the formation of acne or decreasing already established acne comprising esters that hydrolize in the sebaceous glands in combination with an alcohol to prevent hydrolysis of the esters as well as to facilitate the penetration of the ester into the skin, and propylene glycol or glycerol to prevent drying of the skin. The preferred ratio of the constituents is 15 percent to 83 percent to 2 percent respectively.

U.S. Pat. No. 4,664,909 discloses a stable, fast drying pituitous powder deodorant suspension in an alcohol media containing a minimal amount of water and a critical amount of the essential hydroxyethyl cellulose as the suspending agent. The fast drying pituitous suspension of particulate material in an aqueous alcohol media contains hydroxyethyl cellulose at levels above its normal solubility limit by the polyhydric alcohol. The monohydric alcohol constitutes about 55–85 percent; and the water content may be as low as 5 percent if at least 10 percent polyhydric alcohol is also present in the suspension. The combined water and polyhydric alcohol content is at least 15 percent and may be up to about 25 percent. Thus, it is apparent that the proportions of monohydric alcohol, water and polyhydric alcohol are interdependent.

In summary, U.S. Pat. No. 4,664,909 teaches a fast-drying deodorant comprising a critical amount of hydroxyethyl cellose as the deodorant to encapsulate or isolate bacteria to prevent growth of the bacteria, suspended in a solution of monohydric alcohol to provide the fast drying characteristics and polyhydric alcohol to improve the overall solubility of the solution to allow the use of increased levels of monohydric alcohol. The relative proportions of the monohydric alcohol, water and polyhydric alcohol are driven or determined by the desired solubility and therefore are interdependent.

U.S. Pat. No. 3,966,902 disclosed various polymer complex carriers such as propylene glycol for use with an active ingredient such as a disinfectant or fragrance.

U.S. Pat. No. 4,690,779 refers to the use of propylene glycol in combination with alcohol and fragrances. This composition is both toxic and non-biodegradable.

U.S. Pat. No. 4,209,500 teaches a composition suitable for use in aerosol sprays including an anhydrous alcohol and fragrance or perfume. This composition is corrosive, non-biodegradable and non-evaporative.

U.S. Pat. No. 4,689,168 describes a hard surface cleaning composition suitable for glass, chrome, plastic, enamel and other hard surfaces. The composition is applied to the hard surface as an emulsion of an aqueous phase and an oil phase.

The bubbling action is caused by the evaporation of volatile constituents from the film or layer of applied compositions, as well as the desire for the aqueous and oil phase components to reform. The bubbling action, characterized by small bubbles of volatile components erupting from the surface of the composition film aids in lifting soil from the hard surface. As an apparent consequence, the rate of cleaning is accelerated. The composition comprises a polar organic solvent or mixture of solvents, a nonvolatile surfactant, a volatile surfactant such as an acetylenic alcohol or diol, a volatile organosiloxane oligomer and water.

U.S. Pat. No. 5,064,635 describes a mixture of one or more surfactants (detergents) with the pH sensitive dye. The surfactant can be diluted with water to give the desired cleaning strength.

U.S. Pat. Nos. 4,965,063 and 5,057,303 teach compositions similar to that described in U.S. Pat. No. 5,064,635.

U.S. Pat. No. 4,329,334 shows a homogeneous liquid anionic-amphoteric based antimicrobial conditioning shampoo which includes about 0.5 to 2.5 percent of the antimicrobial agent, 1-imidazolyl-1-(4-chlorophenoxy)-3,3-dimethylbutan-2, one, solubilized in an aqueous solution of critical amounts of a mixture of the following specific ingredients: about 10–40 percent by weight of an anionic sulfate or sulfonate surface active agent; about 0.1–7.5 percent by weight of an amphoteric surfactant and about 0.5–2 percent by weight of a lower aliphatic monohydric or polyhydric alcohol or mixtures thereof in certain critical amounts to avoid precipitation of the antimicrobial agent.

U.S. Pat. No. 3,654,165 teaches a cleaner-sanitizer for use on telephone instruments including a fast-acting, penetrative, quick-drying bacteriocidal detergent solution which leaves a safe, active residue of selected proportions of sodium lauryl sulfate, dimethyl sulfone, isopropanol and iodine in solution.

U.S. Pat. No. 4,793,988 describes a composition for disinfecting a surface, such as a public restroom facility or telephone. The composition and delivery of the composition provides for the placement of a thin layer of disinfectant including a dye. The dye disappears as the thin layer effects the germicidal activity of the disinfectant. A sample of the germicidal composition was prepared with 400 mg of sodium dodecyl sulfate (SDS), 400 mg of octyl phenoxy polyethoxyethanol marketed as Triton X-100 and 100 mg of blue dye thymophthalein.

U.S. Pat. No. 4,975,217 describes germicidal compositions for direct application to human skin including an organic acid, and an anionic surfactant, as active ingredients, and can optionally include an alcohol, as an additional active ingredient. When formulated as soaps and lotions, the compositions have been found to produce more than a 2.0 log reduction in bacteria applied to skin. Organic acids and anionic surfactants are used as active ingredients in germicidal products which are applied directly to the skin, such as hand-washing soaps, skin-care lotions, soapy-lotions, or wipes containing these materials.

U.S. Pat. No. 4,046,706 shows a composition for cleaning contact lenses comprising a poly(oxyethylene)-poly(oxypropylene) block copolymer, a water solubility in excess of about 10 gms per 100 ml, a cloud point in 1 percent aqueous solutions above about 30 degrees C, and a foam height in excess of 30 mm; a microbial growth inhibitor; ethyl or isopropyl alcohol; an amphoteric surfactant and water.

U.S. Pat. No. 3,578,499 teaches a powder composition containing a gelling agent, a neutral diluent, a wetting agent and a dye or coloring additive. The powder gelling composition when added to water forms a gel. Acid or alkaline materials are added for cleaning, biocidal agents for sanitizing or other materials to produce a desired effect. The significant advantage of this method is the increased residence time and hence contact time between agents in the gel and the surface to be acted on. A third component included in the gelling composition is a wetting agent exemplified by a linear alkyl benzene sulfonate type material. The wetting agent should be desirably characterized as a anionic agent although it is recognized that nonionic surfactants may also be employed.

U.S. Pat. No. 2,333,124 describes a method for sterilizing air laden with bacteria or other pathogenic organisms comprising contacting the air with a mixture of glycols in vapor form in proportions to provide about 1 gram of such glycols in vapor form to not more than about 5 to 7 million cubic centimeters of air.

U.S. Pat. No. 2,857,315 shows a stable anti-perspirant stick having a base comprising a sodium stearate-propylene glycol soap gel having an active anti-perspirant agent sodium zirconium lactate. The sodium stearate-propylene glycol soap gel may contain alcohol in an amount not substantially greater than the propylene glycol by weight.

Additional examples of the prior art are found in U.S. Pat. Nos. 580,213; 3,282,776; 3,653,499; 3,983,252; 4,004,024; 4,201,764; 4,282,179; 4,265,899; 4,283,421; 4,364,515; 4,436,754; 4,550,105, 4,105,431; 4,122,192; 4,243,403; 4,278,206; 4,322,475; 4,436,732; 4,464,293; 4,597,887, 4,252,694; 4,279,762; 4,325,201; 4,540,505; 4,675,397; 4,937,072; 4,978,530; 4,983,317 and 4,915,934.

Generally these cold chemical sterilants are aqueous (water-based) solutions which contain between 2.0%–4.0% glutaraldehyde designed for one-step, "bucket" sterilization. Glutaraldehyde is a highly unstable, synthetic dialdehyde. It is the two aldehyde groups (one at each end of the molecule) that create or act as the sporicidal mechanism. In use, glutaraldehyde cycles or passes through a five-phase structure equilibrium, of which the dialdehyde structure is only one phase which is sporicidally active phase. As observed, only 12% of glutaraldehyde is in the dialdehyde phase at any one time because of the structural equilibrium. Therefore, if a conventional sterilant's label claim specifies 2.0% glutaraldehyde, there is actually only 0.24% of the active dialdehyde in the solution.

Another major limitation of these conventional sterilants is that the sterilants must be manufactured with an acid pH because acidic glutaraldehyde is relatively stable and can provide the desired three (3) year shelf-life. Moreover, glutaraldehyde is slow to kill spores. In order to render such compositions effective in a real time environment, the pH must be altered to alkaline. The conventional sterilants accomplish this by supplying an activator. The activator does nothing except adjust the glutaraldehyde concentrate or change the solution pH from acidic to alkaline in an effort to enhance the spore kill. However, upon activation the glutaraldehyde gradually polymerizates to render the solution ineffective in 28 days (according to label claims). After activation, conventional glutaraldehyde sterilants require 10–12 hours of direct contact at room temperature to kill bacterial spores.

A principal reason why aqueous, alkaline glutaraldehyde solutions take 10–12 hours to work is because during acceptable sterilization time not enough amino groups are cross-linked (or "fixed" like enbalming fluid works) to effectively kill the spores. This problem is greatly aggravated, however, by the spore's ability to shed that part of the wall being cross-linked. That action by the spore would, for all practical purposes, force the sterilant to restart the entire process with the amino groups on the newly exposed spore wall.

Examination of the prior art reveals most existing compositions available are either toxic or non-biodegradable or both. Toxic chemicals that are not biodegradable contaminate our environment, the soil and the water supply.

In recognition of the dangers of existing disinfectants and sterilants, health facilities are required to notify employees that toxic chemicals are in use, provide special safety equipment and advise them of the possible hazards that result or could result as a consequence of misuse or a spills. Such notices must also be given to the community at large.

Other laws and regulations require users to document the use of toxic chemicals and require that the excess, the waste, and the residue be collected and properly stored. 4 These materials must be collected by licensed and approved toxic waste companies, taken to an authorized disposal site and legally destroyed. The cost of disposing of such toxic material is often more expensive than the initial purchase price.

Sterilants today should be non-toxic or low in toxicity and biodegradable and capable of killing bacterial spores quickly and effectively. Further, such disinfectants and sterilants should be chemically compatible with the numerous apparatus and instruments found in modern healthcare facilities.

As described more fully hereinafter the instant invention is directed to an environmentally safe composition capable of killing anaerobic and aerobic bacteria, *tubercle bacillus*, viruses including the HIV virus, mildew, mold, fungus and bacterial spores. The principal complementary sporicidal ingredients of the invention are selected from a group of monohydric alcohols, a group of polyhydric alcohols, a group of saturated dialdehydes, a group of cationic surface active agents and water.

In the past such alcohols have had limited use outside the laboratory due to various undesirable characteristics of alcohol. For example, it has been universally accepted that alcohol has very limited application as a wipe disinfectant because alcohol is unable to penetrate protein rich material, evaporates quickly, is very stable with infinite shelf life while sealed and has a pungent odor.

The instant invention has evolved from an extensive development program involving the unexpected formulation of certain chemicals to reduce or inhibit those undesirable features of alcohol and to make alcohol safe and effective for use outside the laboratory.

SUMMARY OF THE INVENTION

The present invention relates to a method of immersion sterilization of medical and dental instruments using a manual bucket system or automated sterilization system and an organic cold chemical sterilant capable of killing a challenge of target microorganisms including bacterial spores.

The unique unexpected results of the present invention can best be understood when natural defenses of bacterial spores are examined. In particular, electron microscopy research has shown that a bacterial spore wall is not the dormant, inert shell as once thought. To the contrary, the spore wall is actually a defense mechanism that can shed layers, create barrier material between wall and the nucleus and exhibit motor capabilities. Moreover, there are both structural and functional proteins in the spore including protonated and unprotonated amino groups. In an alkaline, aqueous solution, the outer amino groups on the surface of the spore wall can lose one hydrogen atom ($NH_3 \rightarrow NH_2$) to change from protonated to unprotonated. This phenomenum is important because only the unprotonated ($NH_2$) amino groups act as the reactive sites for dialdehyde molecules to cross-link hydrogen atoms with those amino groups.

The method of immersion sterilization comprises the steps of immersion of the instruments in a first organic solution to reduce bioburden and kill non-spore microorganisms, to solubilize the proteins, and to initiate the cross-linking of unprotonated proteins; immersion of the instruments in an aqueous solution to unprotonate the solubilized proteins and exposing the aqueous solution to an ultrasonic agitation to remove organic material from the instruments; and immersion of the instruments in a second organic solution to complete solubilization of the proteins and cross-linking of unprotonated proteins thereby denaturing the proteins to corrupt and penetrate the bacterial walls to kill the endospores and other microorganisms.

By creating a reverse micelle environment, this invention provides an environment favorable to rapidly kill a challenge of the target microorganisms previously unobserved. A reverse micellar system is a dispersion of spherical droplets of water surrounded and stabilized by a surfactant layer. Each surfactant molecule is composed of a nonpolar tail and a polar headgroup. In a reverse micellar structure, the hydrophobic tails are fully exposed to the organic phase while hydrophilic groups surround water molecules. Some enzymic proteins remain active inside reverse micellies.

The first organic solution includes a monohydric alcohol to kill the non-spore blood borne pathogens in the initial or decontamination step. In addition, a cationic surfactant or surface active agent forms reverse micelles to initiate solubilization of proteins. In addition, a saturated dialdehyde in the first organic solution begins to cross-link unprotonated proteins. In addition a polyhydric alcohol is present to prevent the saturated aldehyde from self polymerizing.

After the initial step of decontamination of the instruments of the non-spore blood borne pathogenic organisms, the instruments are cleaned by immersion in the aqueous solution that may include an effective amount of a surface active agent. Ultrasonic cleaning having the requisite characteristics or parameters of time, frequency and power level is employed to effectively remove any remaining organic material adhering to the instruments. Normal micelles form in the aqueous solution to allow the solubilized proteins to become unprotonated ($NH_3 \rightarrow NH_2$). By losing one hydrogen atom, a reaction site is created favorable for cross-linking in the final step with the second organic solution.

The second organic solution comprises an organic cold chemical sterilant including a composition of interactive constituents having a monohydric alcohol, a polyhydric alcohol, a saturated dialdehyde, a cationic surface active agent and water.

The second organic solution or organic cold chemical sterilant forms reverse micelles to continue the solubilizing of proteins as the saturated dialdehyde cross-links the unprotonated proteins thereby denaturing the proteins to corrupt and penetrate the bacterial walls to kill the endospores and other microorganisms. In addition, the monohydric alcohol acts to kill the non-spore microorganisms to reduce the bioburden on which the saturated dialdehydes must act. The presence of the polyhydric alcohol stabilizes the saturated dialdehyde exponentially increasing the shelf life of the organic cold chemical sterilant from days to months.

Furthermore, the second organic solution may comprise a binary azeotropic composition formed by the chemical bonding between the monohydric alcohol and water in correct proportion to lengthen shelf life, reduce evaporation and the tendency to rust, and enhance efficacy. Specifically, because the azeotrope is stable, the composition will maintain the efficacy for long periods of time. The azeotropic bond between the monohydric alcohol and water causes the combination to evaporate together thus maintaining substantially the same relative concentration of monohydric alcohol and water to retain sufficient potency to kill the target microorganisms. Moreover, because the water is bonded to the monohydric alcohol, the ability to oxidize metal (rust) is greatly reduced. Regardless of extended shelf life, exposure to air in an ultrasound, or carelessness with regard to keeping containers tightly sealed, the concentration of monohydric alcohol necessary for passing the government testing protocols will be maintained.

The invention accordingly comprises the features of construction, combination of elements, and arrangement of parts which will be exemplified in the construction hereinafter set forth, and the scope of the invention will be indicated in the claims.

DETAILED DESCRIPTION OF THE PREFERRED EMBODIMENT

Various sterilizing compositions and delivery systems have been developed to kill a wide range of microorganisms including bacterial spores. The application or use of such sterilizing compositions or sterilants is generally limited by the chemical and biological effect of such compositions on the surfaces and delivery means exposed to such compositions.

The present invention relates to a method of immersion sterilization of medical and dental instruments using a manual bucket system or automated sterilization system and an organic cold chemical sterilant capable of killing a challenge of target microorganisms including bacterial spores.

As described more fully hereinafter, the method of immersion sterilization comprises the steps of immersion of the instruments in a first organic solution to solubilize the proteins, immersion in an aqueous solution to unprotonate the solubilized proteins and exposing the instruments to ultrasonic agitation to remove organic material therefrom, and immersion in a second organic solution to cross-link the unprotonated proteins thereby denaturing the proteins to corrupt and penetrate the bacterial walls to kill the endospores and other microorganisms.

The first organic solution or disinfectant comprises a composition including a monohydric alcohol, polyhydric alcohol optionally, a dialdehyde, a cationic sufactant and water combined in relative proportions by weight to disinfect or decontaminate medical and dental instruments and other devices such as scopes and dental handpieces. The application of the disinfectant is capable of killing a challenge of the target of microorganisms discussed herein.

The aqueous solution comprises a composition including a surface active agent and water.

The organic cold chemical sterilant or second organic solution comprises a composition including a monohydric alcohol, polyhydric alcohol, dialdehyde, cationic surfactant and water combined in relative proportions by weight to sterilize medical and dental instruments and other devices such as scopes and dental handpieces. The organic cold chemical sterilant is capable of killing a challenge of target microorganisms discussed herein within ten minutes.

The monohydric alcohols are selected from the group consisting of isopropyl, methyl, ethyl, n-propyl, n-butyl, tert-butyl and allyl and mixtures thereof. The preferred monohydric alcohol is isopropyl.

The polyhydric alcohols are selected from the group consisting of propylene glycol; 1,3 propanediol; 1,2 butanediol, polyethylene glycol, glycerol, 1,4 butanediol, diethylene glycol and triethylene glycol and mixtures thereof. The preferred polyhydric alcohol is polyethylene glycol with a molecular weight of 400 or less. Polyethylene glycols, which are designated by a number that represents the average molecular weight, range from clear viscous liquids at room temperature, PEGs 200, 300, 400 and 600, to soft solids PEGs, 1000 and 1450, to waxy solids available in the form of flakes or powders, PEGs 3350, 8000 and 14000.

The dialdehydes are selected from the group consisting of malonaldehyde, succinaldehyde, oxaldehyde (glyoxal), adipaldehyde and preferably, glutaraldehyde.

The surface active agents are selected from the group consisting of methylbenzethonium chloride, dodecylamine, hexadecylamine, hexadecylamine hydrochloride, dodecyl aniline, oleyl methylamine ethylene diethylamine methyl sulfate, oleyl benzylamino ethylene diethyamine hydrochloride, sulfate of lauryl pyridinium, octadecyl methylene pyridinium acetate, methyl sulfate of dimethyloctadecyl sulfonium, betaine compound of diethyl aminoacetic acid, octadecyl chloromethyl ether, cetylpyridinium bromide, dodecyltrimethylammonium bromide, hexadecyltrimethylammonium bromide, tetradecyltrimethylammonium bromide, benzalkonium chloride, benzethonium chloride, benzyldimethyldodecylammonium bromide, benzyldimethylhexadecylammonium chloride, benzyldimethyltetradecylammonium chloride, benzyltrimethylammonium methoxide, cetyldimethylethylammonium bromide, decamethonium bromide, dimethyldioctadecylammonium bromide, methylbenzethonium chloride, methyl mixed trialkylammonium chloride, methyltrioctylammonium chloride, 4-picoline dodecyl sulfate, n,n,n'poloxyethylene (10)-n-tallow-1,3-diamino propane and preferably cetylpyridinium chloride.

As used herein, the term target pathogenic organisms refers to Bacteria—spores (*Bacillus subtilis* and *Clostridium sporogenies*), Tubercle Bacillus (*mycobacterium bovis*) and vegetative cells (*Pseudomonas aeruginosa, Salmonella chloraesius* and *Staphylococcus aureus*); Fungi— (*Trichophyton mentagrophytes*); and Virus—nonlipid and small (Polio virus) and lipid and medium size (Herpes simplex 2 and HIV).

As used herein, the term non-toxic refers to the acute dermal, acute inhalation and acute oral dosage as defined in Sub Part 2, Appendix A to 29 Code of Federal Regulations 1910.1200.

As used herein, the term biodegradable refers to decomposition in the presence of 25 percent organic material within 90 days at 69 degrees F (Standard Temperature) with moisture content of 100 parts per million.

As used herein, the term challenge refers to a test colony or specimen of $10^6$ specified target pathogenic organisms.

As used herein, the term hypocompatible means no significant or debilitating degradation effects to the materials and surfaces listed below when exposed to the composition for an extended period including for example, discoloration, corrosion, cracking, and embrittlement. The materials and surfaces tested exhibiting no detectable change. including: Buna-N, Neoprene, natural rubber, upholstery material, white styrene, counter top laminate, natural polypropylene, natural Teflon, natural HDPE, brushed aluminum, bright aluminum, clear Lexan, natural ABS, natural nylon, assorted dental instruments, Tygon tubing, nylon reinforced vinyl tubing, epoxy coated steel and painted steel. In addition, the following instruments were tested with the organic cold chemical sterilant with no observable damage to instruments, the finish or functions including locking cotton pliers, aspirating syringe, universal forceps, Perio probe, mirror head, root tip pick and hemostat.

As used herein, the term azeotropic means a constant boiling liquid admixture of two or more substances, whose admixture behaves as a single substance, in that the vapor, produced by partial evaporation or distillation of the liquid has the same composition as the liquid, i.e., the admixture distills without substantial composition change. Constant boiling compositions, which are characterized as azeotropic, exhibit either a maximum or minimum boiling point, as compared with that of the nonazeotropic mixtures of the same substances.

As used herein, the term organic means the presence of less than about 10 percent by weight of free water within a solution containing carbon base molecules.

As used herein, the term aqueous means the presence of more than about 10 percent by weight of free water within a solution.

The specific monohydric alcohols, polyhydric alcohols, dialdehyde and surface active agent and relative ratios together with the water component complement and interact synergistically to create the desired solubility, specific gravity, conductivity, pH, flash point, boiling point and evaporation required for the effective use of the organic cold chemical sterilant against the challenge as defined herein on microorganisms as described herein and with a hypocompatible effect as defined herein on the surfaces described herein.

Further, the polyhydric alcohol reduces the harmful effects of composition if swallowed or sprayed into the eyes or on mucus membranes as well as soothing the skin upon contact. Tests indicate that the polyhydric alcohol increases the overall effectiveness of the composition against most viruses, mold and mildew and bacterial spores.

Since the organic cold chemical sterilant was developed for use on a wide variety of instruments and devices the measure of chemical resistance is important to permit broad use and application. To be effective, the organic cold chemical sterilant must be hypocompatable.

The method of the present invention comprises: decontaminating the instruments by immersion in the first organic solution including a monohydric alcohol and polyhydric alcohol to kill the non-spore blood borne pathogens, a cationic surfactant to form reverse micelles to initiate solubilization of the proteins of the spore walls and a dialdehyde to begin cross-linking unprotonated amino groups on the spore walls; cleaning the instruments by immersion in an aqueous solution and applying ultrasonic sound having the requisite characteristics or parameters of time, frequency and power level to the instruments to effectively remove remaining organic material adhering to the instruments; and immersion of the instruments in the second organic solution or organic cold chemical sterilant including the cationic surfactant to form reverse micelles to continue the solubilizing of the proteinaceous spore wall as the saturated dialdehyde continues cross-linking the unprotonated proteins thereby denaturing the proteins to corrupt and penetrate the bacterial and conidial walls to kill the endospores and other microorganisms. The aqueous solution may contain an effective amount of cationic surfactant to form normal micelles.

Comparative results of the organic cold chemical sterilant with the individual constituents have demonstrated that the combination of interactive ingredients provides a cold chemical sterilant compatible with an expansive range of materials found in a wide variety of environments.

In order to accomplish the design criteria of a hypocompatible organic cold chemical sterilant effective against the wide range of target microorganisms described herein, the composition should have a pH of between about 6.0 and 7.5 or essentially neutral, have an effective kill time of about 8 to 12 minutes and minimize toxic residue.

Standard Association of Official Analytical Chemists (A.O.A.C.) tests of the instant method have been conducted against the target microorganisms described herein including spores of *Bacillus subtilis*, *Clostridium sporogenes*. The organic cold chemical sterilant has killed the target microorganisms within ten minutes.

The effective proportional relationship of the ingredients by weight of the first organic solution or disinfectant for the monohydric alcohol is between about 65 percent to about 75 percent, for the polyhydric alcohol is between about 4 percent and about 16 percent and for the cationic surface active agent is between about 0.1 to about 2.0 percent, and for the water is between about 9 percent and about 20 percent. The disinfectant may also include by weight a saturated dialdehyde between about 0.1 to about 2.0 percent.

The preferred proportional relationship of the ingredients by weight of the disinfectant is about 70 percent for the monohydric alcohol, between about 8 to about 12 percent for the polyhydric alcohol, and between about 0.5 to about 1.0 percent for the cationic surface active agent and between about 16 to about 20 percent for the water. The disinfectant may further include by weight a saturated dialdehyde between about 0.5 to about 1.0 percent. As a result there is reduced dermal toxicity. In addition, since there is minuscule electrolytic activity there is no significant positive interaction between the composition and the instruments.

The effective proportional relationship of the ingredients by weight of the organic cold chemical sterilant for the monohydric alcohol is between about 65 percent to about 75 percent, for the polyhydric alcohol is between about 4 percent and about 16 percent and for both the saturated dialdehyde and the cationic surface active agent is between about 0.1 to about 2.0 percent, and for the water is between about 9 percent and about 20 percent.

The preferred proportional relationship of the ingredients by weight is about 70 percent for the monohydric alcohol, between about 8 to about 12 percent for the polyhydric alcohol, and between about 0.5 to about 1.0 percent for both the saturated dialdehyde and cationic surface active agent and between about 14 to about 18 percent for the water.

The first and second organic solution each comprises a binary azeotropic composition formed by the chemical bonding between the monohydric alcohol and water in correct proportion to lengthen shelf life, reduce evaporation and the tendency to rust, and enhance efficacy. Specifically, because the azeotrope is stable, the composition will maintain the efficacy for long periods of time. The azeotropic bond between the monohydric alcohol and water causes the combination to evaporate together thus maintaining substantially the same relative concentration of monohydric alcohol and water to retain sufficient potency to kill the target organisms. Moreover, because the water is bonded to the monohydric alcohol, the ability to rust metal is greatly reduced. Thus, after registering significant amounts of evaporation in laboratory tests, presumed loss of efficacy would be expected. Because of the azeotrope however, even after a 33 percent weight loss, the concentration of monohydric alcohol was still at 66 percent. Therefore, most of the evaporation was from the free water with a portion of the azeotropic monohydric alcohol. Regardless of extended shelf life, exposure to air in an ultrasound, or carelessness with regard to keeping containers tightly sealed, the required concentration of monohydric alcohol essential to achieve accepted and required testing protocols will be maintained.

In the total concentrations used in the solutions about 70 percent monohydric alcohol requires about 10 percent water to be azeotropic. To provide the ability to kill the hydrophobic organisms, additional amounts of water up to about 10 percent or an amount equal to the azeotropic equilibrium for an upper limit of 20 percent water by weight may be added without degradation of the monohydric alcohol/water azeotrope.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A method of immersion sterilization of medical and dental instruments to kill a challenge of target microorganisms including bacterial spores, said method of immersion sterilization comprises the steps of immersion of the instruments in a first organic solution comprising about 65 percent to about 75 percent by weight of a monohydric alcohol selected from the group consisting of isopropyl, methyl, ethyl, n-propyl, n-butyl and allyl and mixtures thereof, about 4 percent to about 16 percent by weight of a polyhydric alcohol selected from the group consisting of propylene glycol; 1,3 propanediol; 1,2 butanediol, polyethylene glycol; glycerol and 1,4 butanediol and mixtures thereof, and about 0.1 percent to about 2.0 percent by weight of a cationic surfactant to solubilize the protein of the microorganisms, immersion in an aqueous solution and applying ultrasonic sound having the parameters of time, frequency and power to effectively remove organic material from the instruments and immersion in an organic cold chemical sterilant comprising about 65 percent to about 75 percent by weight of a monohydric alcohol selected from the group consisting of isopropyl, methyl, ethyl, n-propyl, n-butyl, tert-butyl and allyl and mixtures thereof and about 4 percent to about 16 percent by weight of a polyhydric alcohol selected from the group consisting of propylene glycol; 1,3 propanediol; 1,2 butanediol, polyethylene glycol; glycerol and 1,4 butanediol and mixtures thereof, about 0.1 percent to about 2.0 percent by weight of a dialdehyde selected from the group consisting of malonaldehyde, succinaldehyde, oxaldehyde (glyoxal), adipaldehyde and glutaraldehyde and about 0.1 percent to about 2.0 percent by weight of a cationic surfactant to cross-link at the binding sites of unprotonated proteins thereby denaturing the proteins to corrupt and penetrate the bacterial and conidium walls to kill the endospores and other microorganisms wherein the pH of said organic cold chemical sterilant is between about 6.0 to about 7.5.

2. The method of immersion of sterilization of medical and dental instruments of claim 1 wherein the preferred proportional relationship of the ingredients by weight of said first organic solution is about 70 percent for the monohydric alcohol and between about 0.5 to about 1.0 percent for the cationic surfactant.

3. The method of immersion sterilization of medical and dental instruments of claim 1 wherein said organic cold chemical sterilant further includes between about 14 percent to about 18 percent by weight of water.

4. The method of immersion sterilization of medical and dental instruments of claim 1 wherein said first organic solution further includes about 9 percent to about 20 percent of water by weight.

5. The method of immersion sterilization of medical and dental instruments of claim 1 wherein said first organic solution further includes about 0.1 to about 2.0 percent by weight a saturated dialdehyde.

6. The method of immersion sterilization of medical and dental instruments of claim 5 wherein the preferred amount by weight of said saturated dialdehyde is between about 0.5 to about 1.0 percent.

7. The method of immersion sterilization of medical and dental instruments of claim 5 wherein the preferred proportional relationship of the ingredients by weight of said organic cold chemical sterilant is about 70 percent for the monohydric alcohol, between about 8 to about 12 percent for the polyhydric alcohol, and between about 0.5 to about 1.0 percent for both the saturated dialdehyde and cationic surfactant.

8. The method of immersion sterilization of medical and dental instruments of claim 1 wherein said aqueous solution further includes an effective amount of a cationic surfactant to unprotonate the solubilized proteins.

* * * * *